United States Patent
Hen et al.

(10) Patent No.: US 8,007,833 B2
(45) Date of Patent: Aug. 30, 2011

(54) METHOD OF REDUCING INFECTIONS AND/OR AIR EMBOLISMS ASSOCIATED WITH VASCULAR ACCESS PROCEDURES

(75) Inventors: John Hen, Bradenton, FL (US); Roger Thomas, Pinehurst, NC (US); Griscom Bettle, Sarasota, FL (US); Timothy J. Kelly, Sarasota, FL (US)

(73) Assignee: Biolife, L.L.C., Sarasota, FL (US)

( * ) Notice: Subject to any disclaimer, the term of this patent is extended or adjusted under 35 U.S.C. 154(b) by 4 days.

(21) Appl. No.: 12/557,102

(22) Filed: Sep. 10, 2009

(65) Prior Publication Data

US 2011/0060295 A1   Mar. 10, 2011

(51) Int. Cl.
*A01N 59/16* (2006.01)
*A61M 31/00* (2006.01)
*A61M 37/00* (2006.01)
*A61B 17/20* (2006.01)

(52) U.S. Cl. ............... 424/646; 604/506; 604/46

(58) Field of Classification Search .......... None
See application file for complete search history.

(56) References Cited

U.S. PATENT DOCUMENTS

| | | | |
|---|---|---|---|
| 4,917,112 A * | 4/1990 | Kalt ............................ | 602/58 |
| 6,187,347 B1 * | 2/2001 | Patterson et al. ............ | 424/646 |
| 6,267,896 B1 | 7/2001 | Patterson et al. | |
| 6,521,265 B1 | 2/2003 | Patterson | |
| 2007/0225652 A1 * | 9/2007 | Scherr ........................ | 604/180 |
| 2008/0014251 A1 * | 1/2008 | Benz et al. .................. | 424/445 |
| 2009/0252799 A1 | 10/2009 | Hen et al. | |

* cited by examiner

*Primary Examiner* — Nicholas D Lucchesi
*Assistant Examiner* — Pritesh Patel
(74) *Attorney, Agent, or Firm* — Charles J. Prescott

(57) ABSTRACT

A method of reducing infections associated with vascular access procedures. A powder containment device (PCD) is preferably adhesively attached to a skin area, the PCD having a hole formed centrally therethrough adapted to completely surround the catheter wound site. The open cavity formed by the PCD being attached to the skin is filled with a hemostatic agent of a salt ferrate and an insoluble cation exchange material. The salt ferrate combines with blood to form a trivalent $Fe^{+++}$ ion promoting blood clotting and producing oxygen at the wound site for bacteria reduction. The cation exchange material also forms a protective cover over the wound site as the trivalent $Fe^{+++}$ ion is formed. Semi-occlusive pressure is applied against the hemostatic agent for a time sufficient to arrest blood flow from the wound site right after inserting or removing the catheter. The PCD and hemostatic agent are then covered with an adhesive dressing. The occurrence of air embolisms introduced around the catheter is also reduced after the hemostatic agent has interacted to arrest blood flow around the catheter.

5 Claims, 15 Drawing Sheets

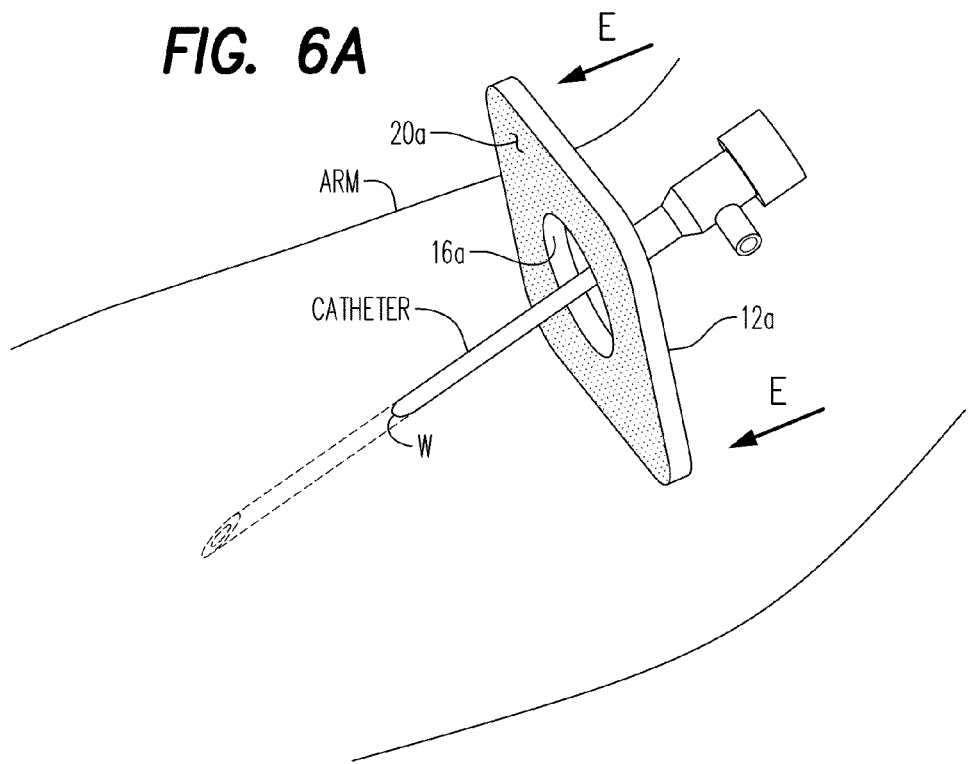
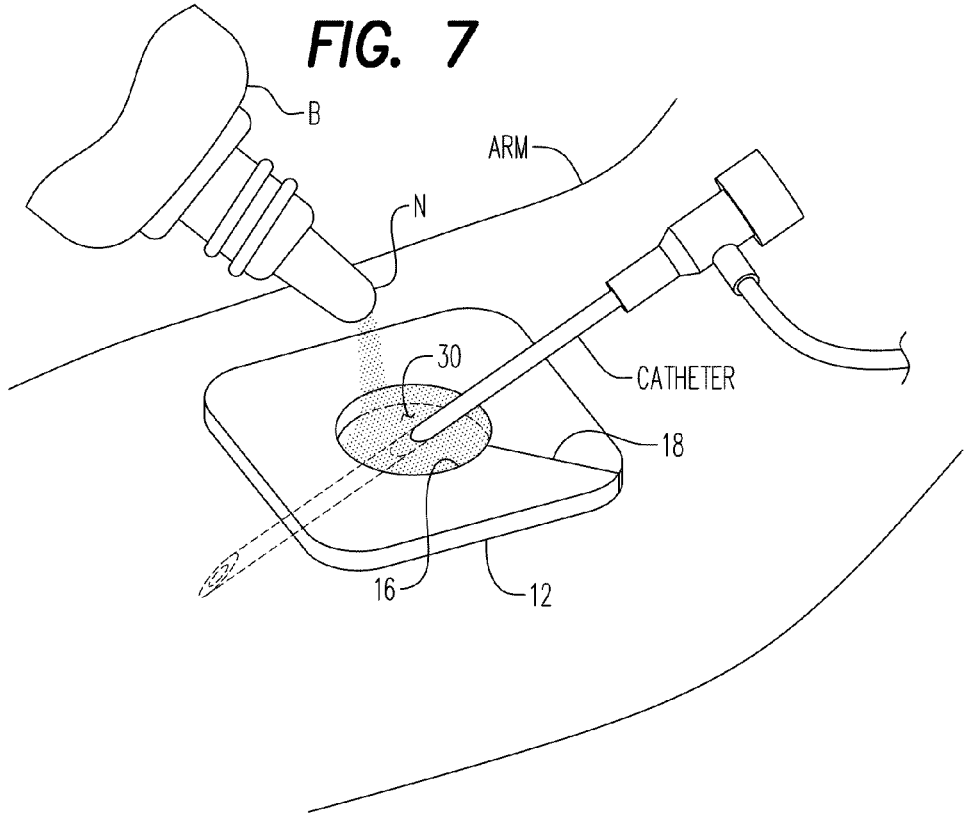

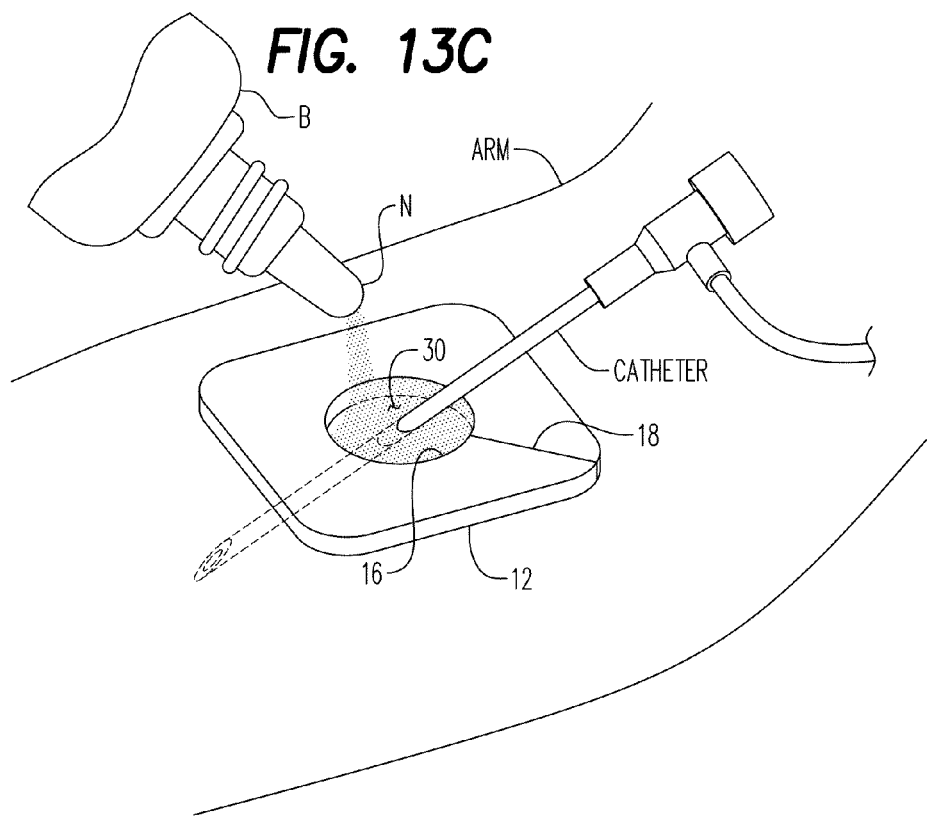
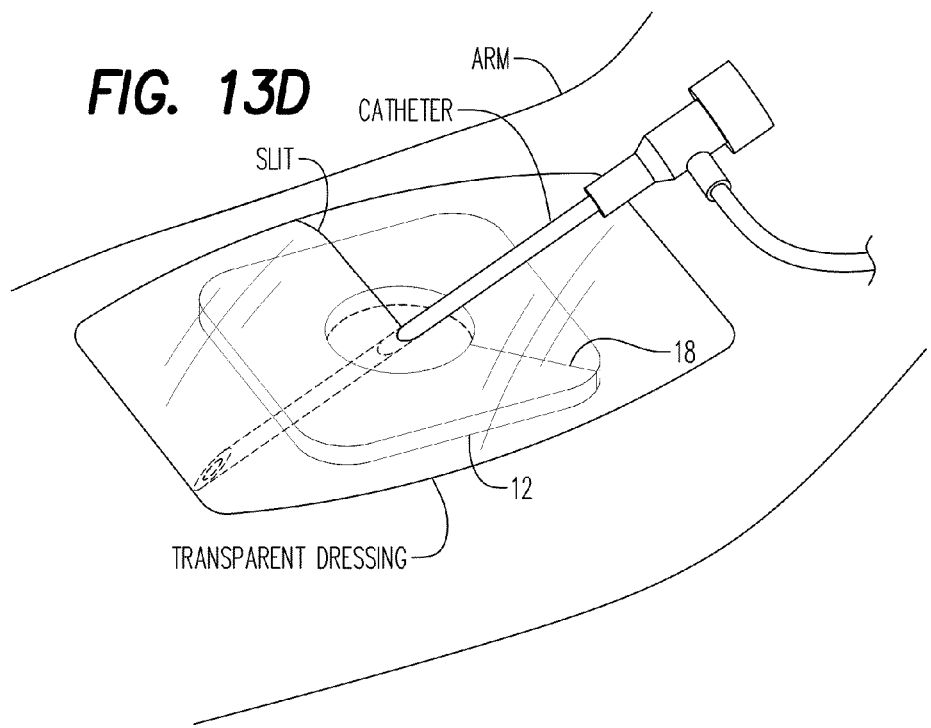

ly therethrough adapted to completely surround the catheter wound site. The open cavity formed by the PCD being attached to the skin is filled with a hemostatic agent (dry powder or particles) of a salt ferrate and an insoluble cation exchange material. The salt ferrate combines with blood to form a trivalent $Fe^{+++}$ ion promoting blood clotting and producing oxygen at the wound site for bacteria reduction.

METHOD OF REDUCING INFECTIONS AND/OR AIR EMBOLISMS ASSOCIATED WITH VASCULAR ACCESS PROCEDURES

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to techniques for catheter (or cannula) insertions or removals during, vascular access procedures, and more particularly to a method of reducing infections and/or air embolisms associated therewith.

2. Description of Related Art

The insertion of a catheter (sometimes referred to as a cannula) into the vein or artery of a patient to effect fluids and medicine delivery and blood sample monitoring has been historically problematic for causing internal infections within the patient. The presence of a blood or systemic infection will typically make its presence felt either when the catheter is left in place for an extended period of time, or after it is removed. This is not only a problem in outpatient settings, but also within an acute care and emergency room settings of a hospital. Once an infection is identified, the only treatment available is to begin an appropriate antibiotics regime until the infection has been overcome.

A composition for arresting the flow of blood or another protein containing blood fluids flowing from an open wound has been patented by Patterson et al. in U.S. Pat. No. 6,187,347 teaching a substantially anhydrous compound of a salt ferrate which will hydrate in the presence of blood and body fluid to produce $Fe^{+++}$ promotes clotting when applied directly over a wound and forming a protective scab attached to the wound to enhance healing thereof. Oxygen is also produced during the reaction.

One aspect of the present invention utilizes the heretofore unrealized virtues of the '347 compound in conjunction with the installation of a catheter and other types of vascular access procedures both at the time of catheter insertion and at the time of removal of the catheter from the vein or artery and skin area of the patient.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This disclosure is directed to a method of reducing infections associated with catheter installations and removals. A powder containment device (PCD) (preferred) is adhesively attached to a skin area, the PCD having a hole formed centrally therethrough adapted to completely surround the catheter wound site. The open cavity formed by the PCD being attached to the skin is filled with a hemostatic agent (dry powder or particles) of a salt ferrate and an insoluble cation exchange material. The salt ferrate combines with blood to form a trivalent $Fe^{+++}$ ion promoting blood clotting and producing oxygen at the wound site for bacteria reduction.

The salt ferrate described in this disclosure is also a powerful short term anti-microbial (hours). Longer-term anti-microbial effects (days) are due to the hydrogen cation exchange resin, and the low pH (~2) environment (lower than the natural acid mantle of the skin) which it generates on the skin surface (when wetted) around the catheter. The pH under the seal (scab) is neutral (7.4). In addition, the powder is preferably at least about 2 mm (0.08") deep around the catheter and the wetness of the powder is asymmetric in depth (wet on the skin, dry on top). This surface dry powder is an extremely powerful desiccant, and is a hostile environment to any invading bacteria by means of dehydrating the bacteria. The preferred use of a PCD helps to attain the effect of having dry powder on top; because it is dry, the pH is unmeasurable.

The cation exchange material also forms a protective cover over the wound site as the trivalent $Fe^{+++}$ ion is formed during catheter insertion and after catheter removal. Semi-occlusive pressure is applied against the hemostatic agent around the catheter for a time sufficient to arrest blood flow from the wound site. The PCD is then covered with an adhesive dressing. The hemostatic agent (powder) may also be used with a partially encircling PCD or without a PCD and the microbial protection and the reduction of air embolisms are identical. It is applied around the catheter, and then a semi-occlusive pressure is applied with gloved fingers (or non-stick dressing between fingers and powder). The powder "pile" area is then covered with an adhesive dressing. The PCD makes the application of the powder much neater and more convenient, with less powder loss. Note that this disclosed procedure is equally effective for microbial protection at the onset of a vascular access procedure by being applied around the catheter promptly after insertion into the vein or artery.

It is therefore an object of this invention to provide an improved method of installing and removing catheters from patients during vascular access procedures which will substantially reduce or eliminate the occurrence of blood and systemic infections in a patient undergoing such a procedure.

Still another object of this invention is to take advantage of the heretofore unknown antimicrobial features of the compound taught in U.S. Pat. No. 6,187,347 in conjunction with the installation of catheters and any vascular access procedures.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

Figure 1:
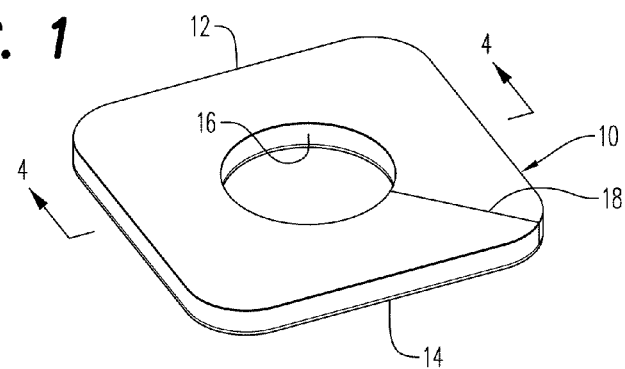
FIG. 1 is a perspective view of one embodiment of a powder containment device (PCD).
Figure 2:
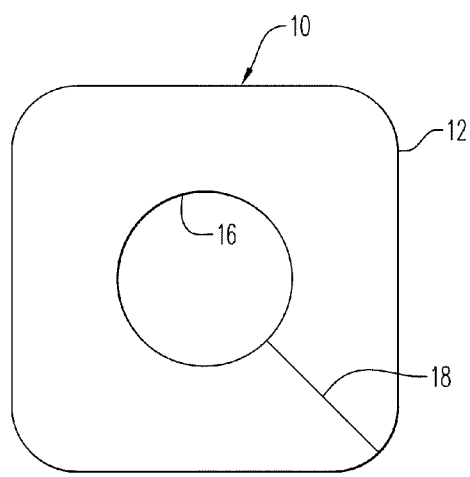
FIG. 2 is a top plan view of FIG. 1.
Figure 3:
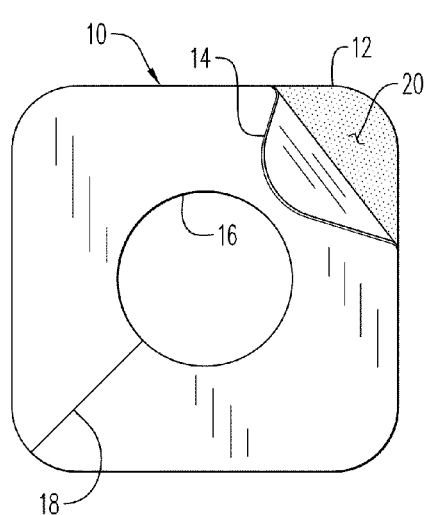
FIG. 3 is a bottom plan view of FIG. 1 showing the partial removal of an adhesive protective cover thereof.
Figure 4:
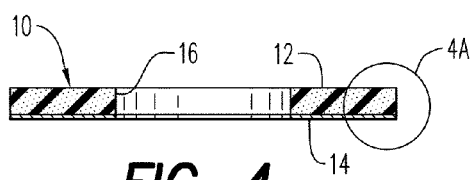
Figure 4A:
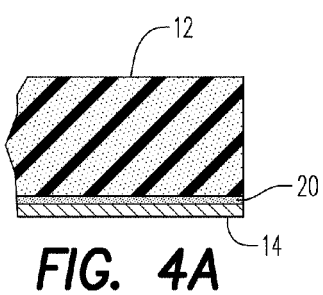
Figure 5:
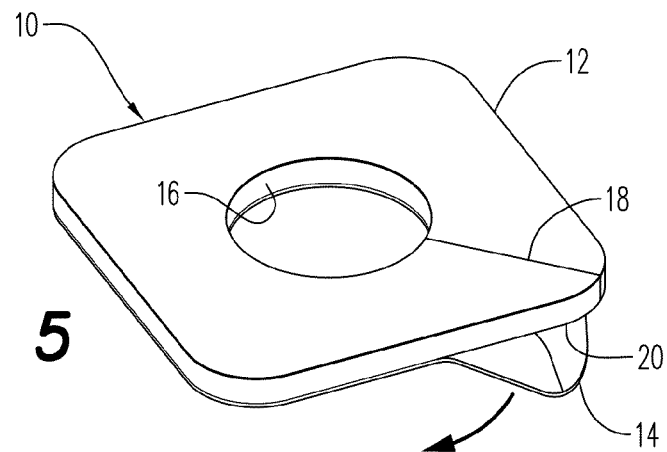
Figure 6:
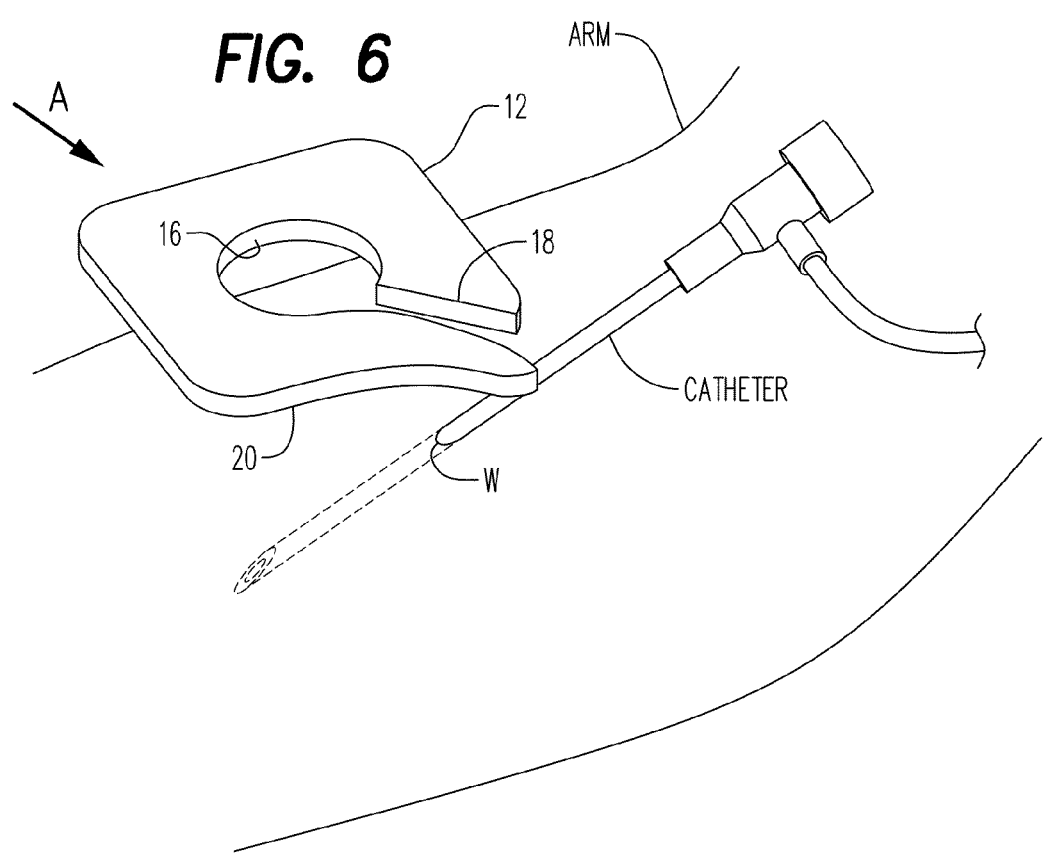
Figure 7A:
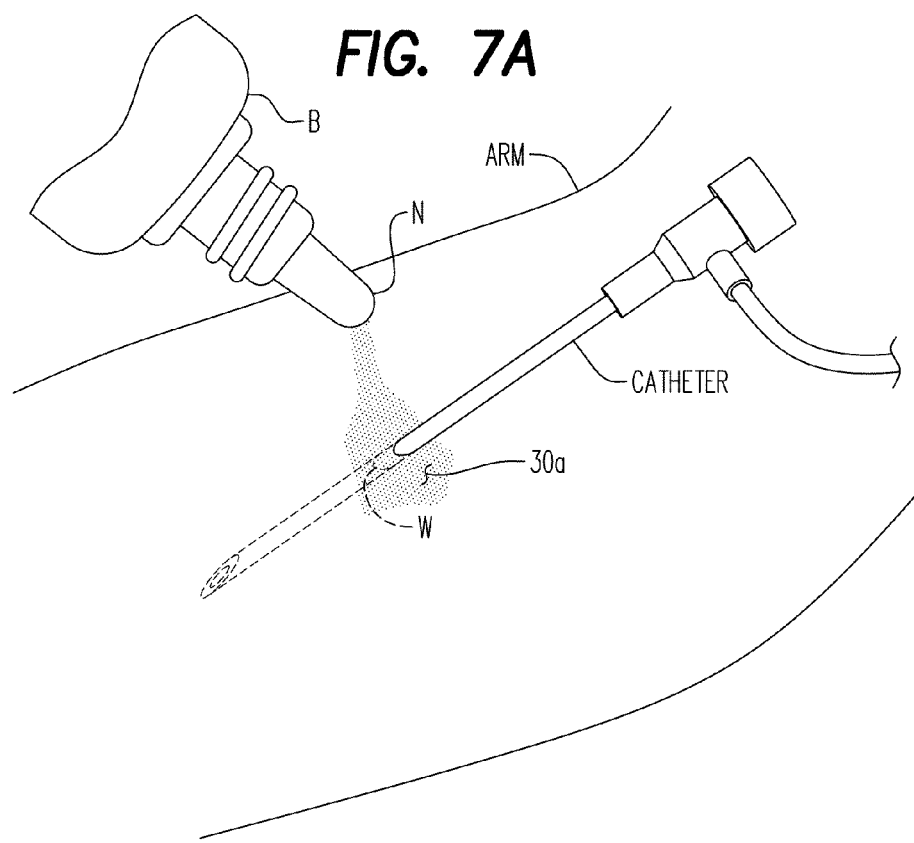
Figure 8:
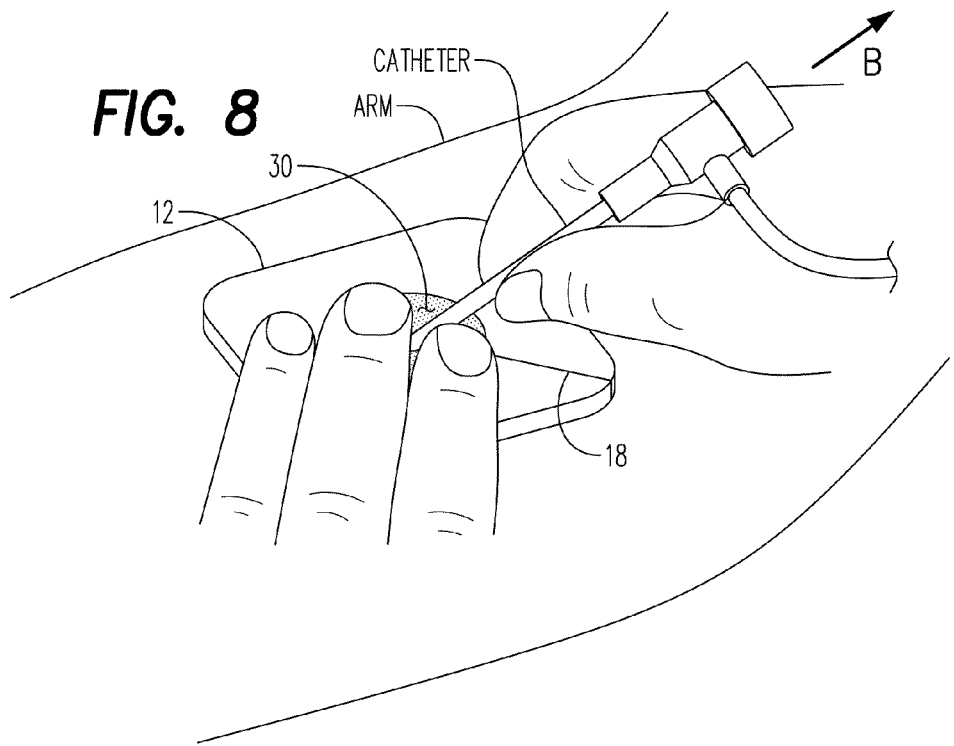
Figure 9:
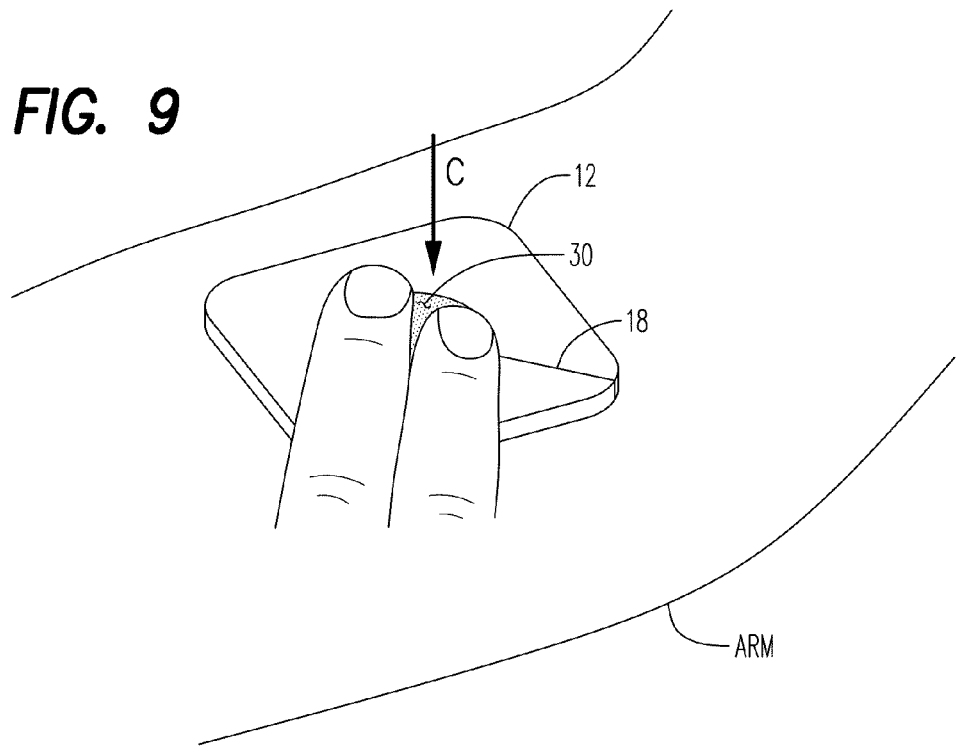
Figure 9A:
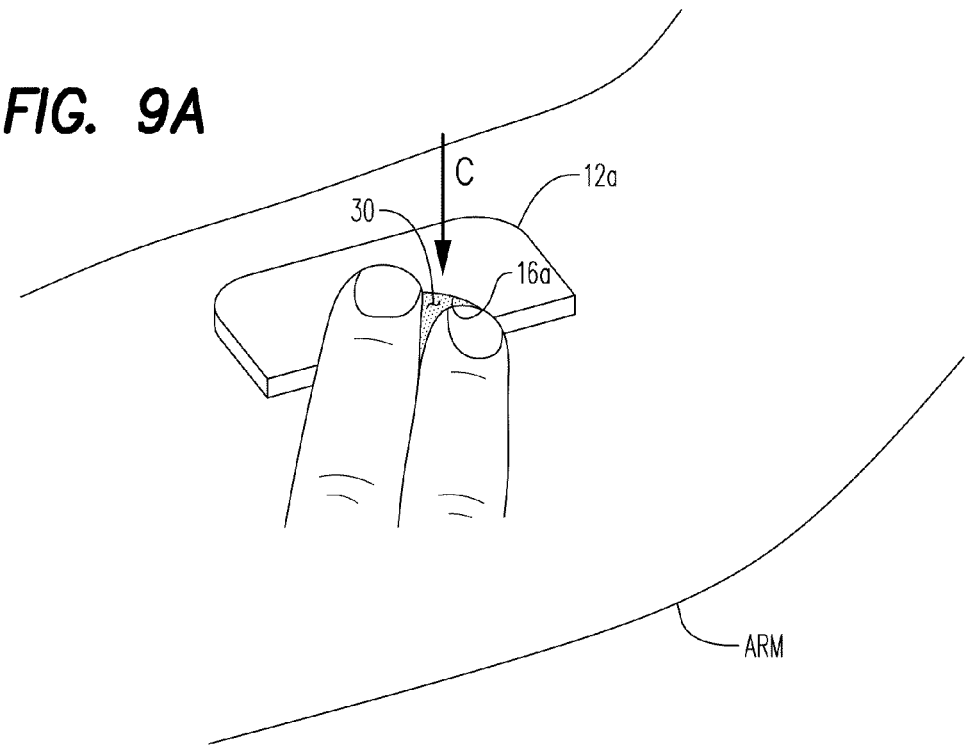
Figure 10:
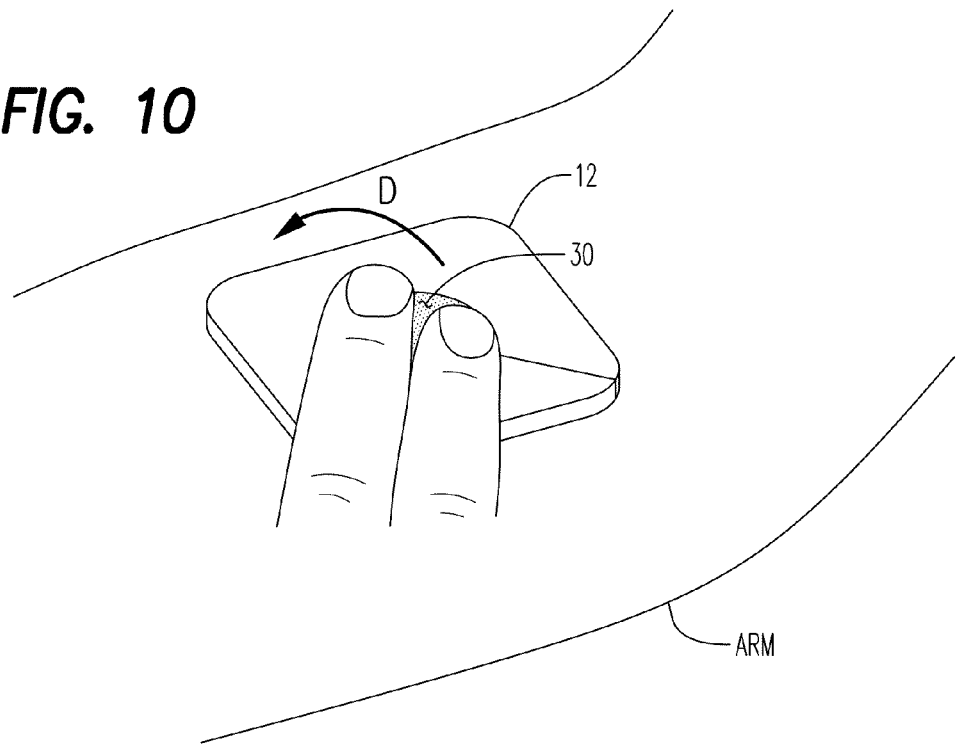
Figure 11:
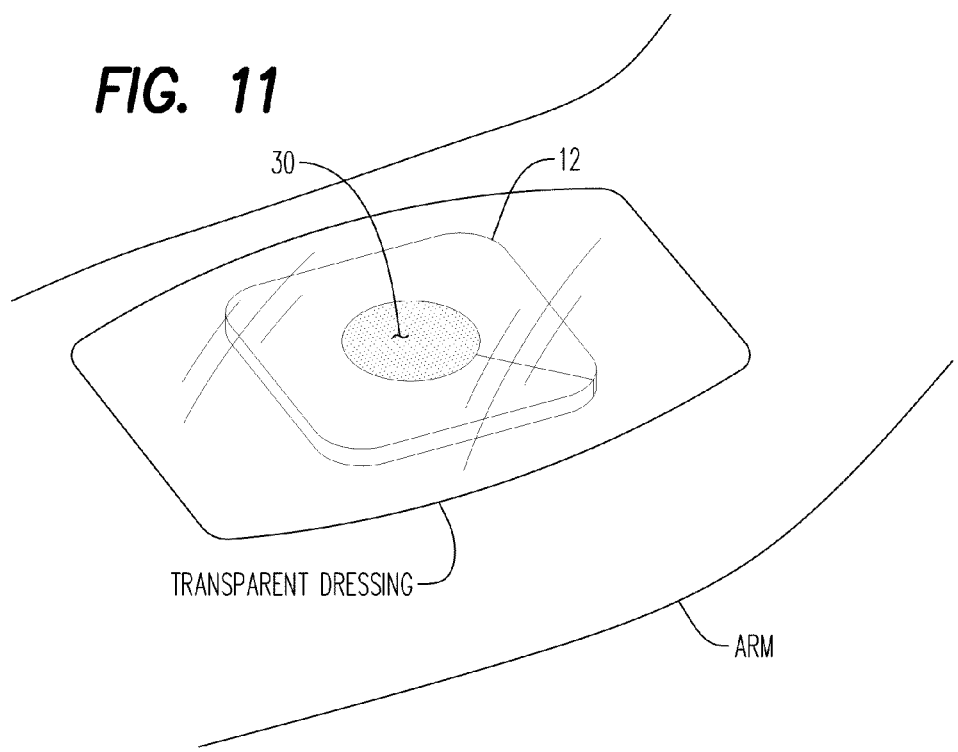
Figure 11A:
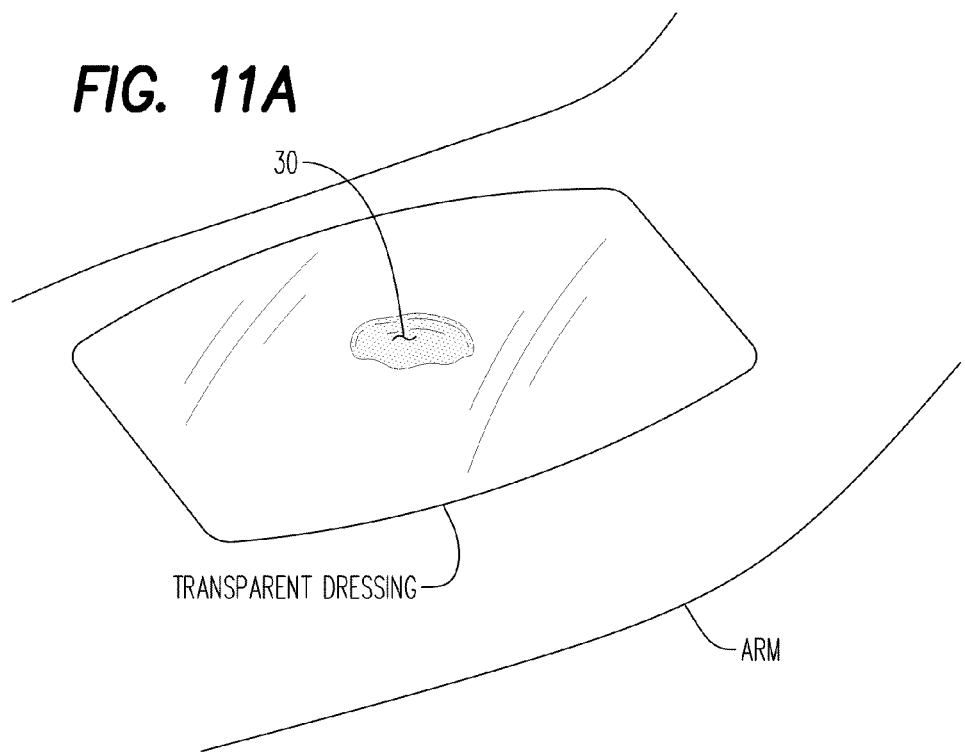
Figure 12:
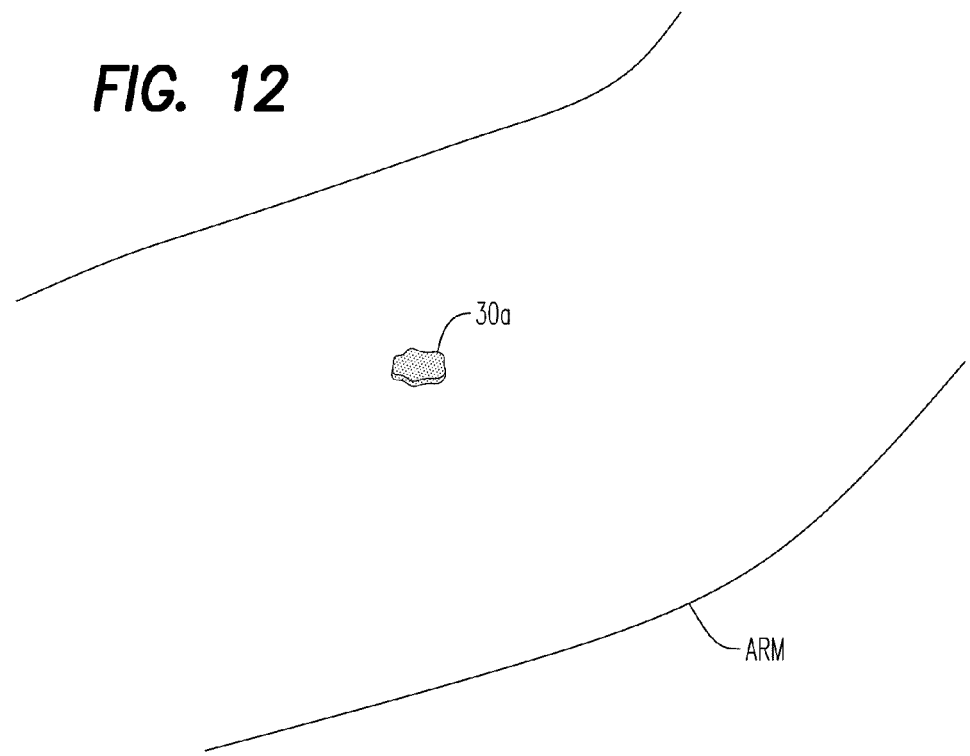
Figure 13A:
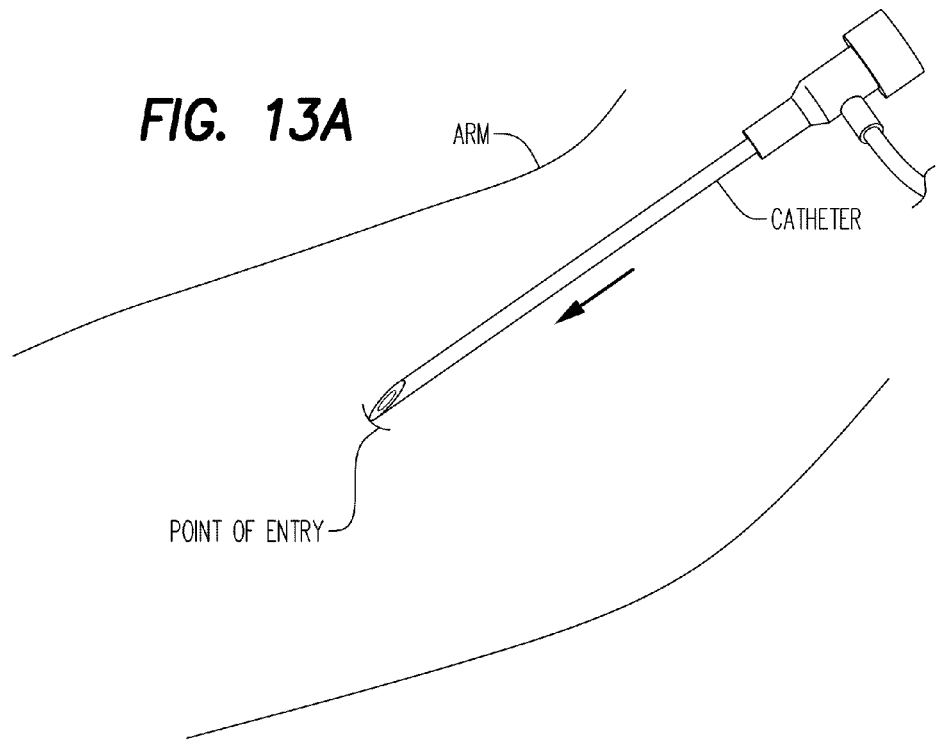
Figure 13B:
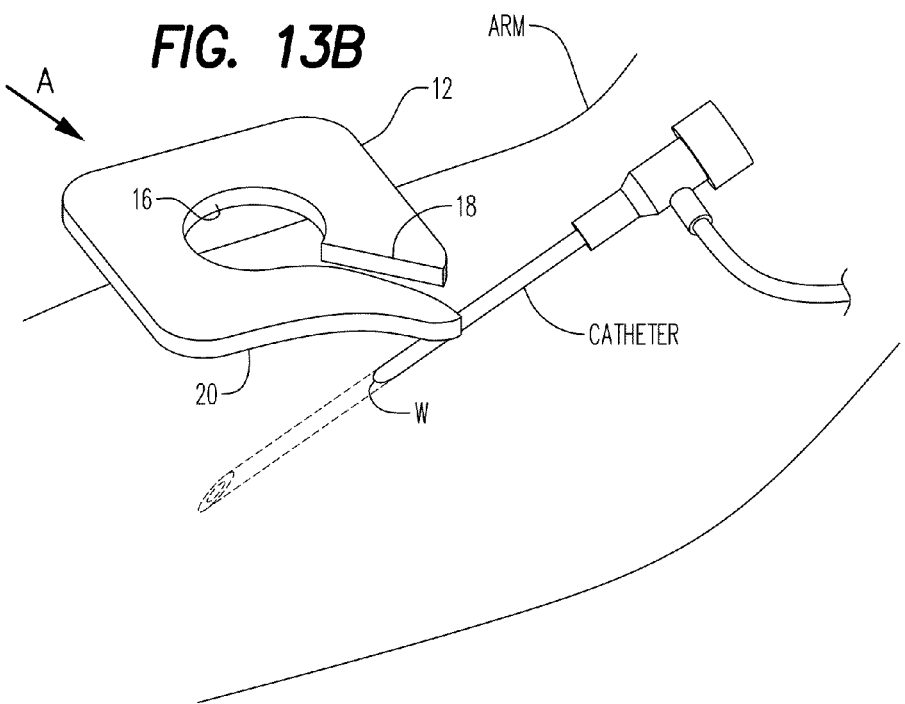
Figure 14:
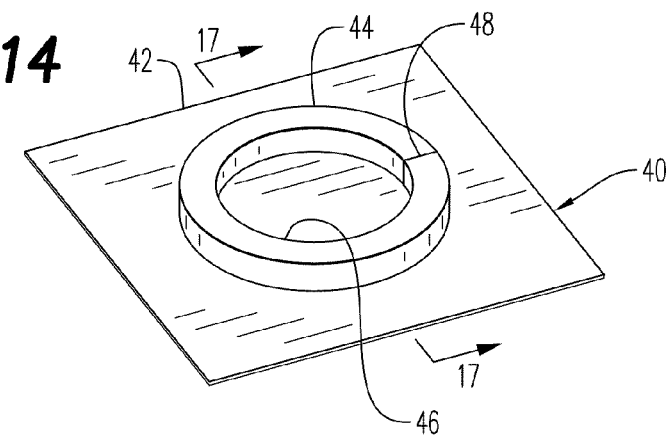
Figure 15:
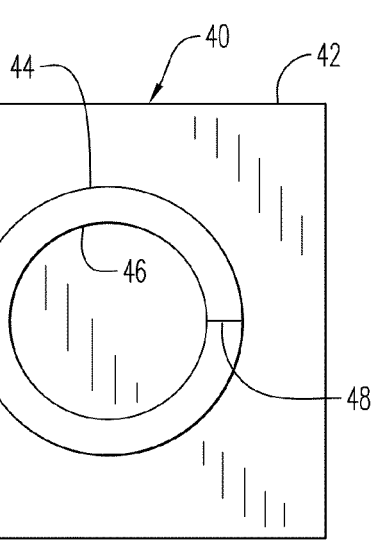
Figure 16:
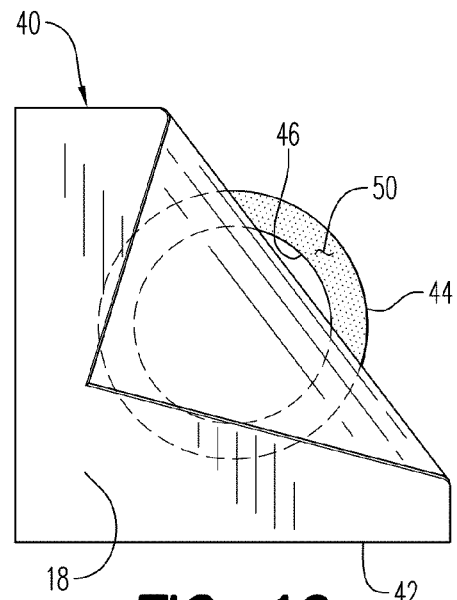
Figure 17:
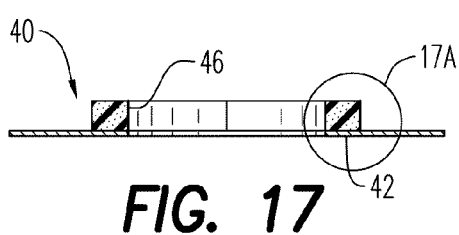
Figure 17A:
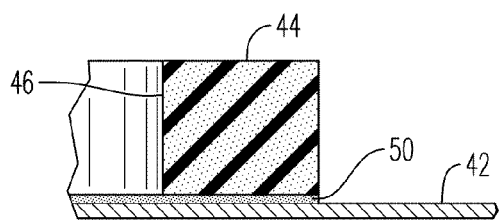
Figure 18:
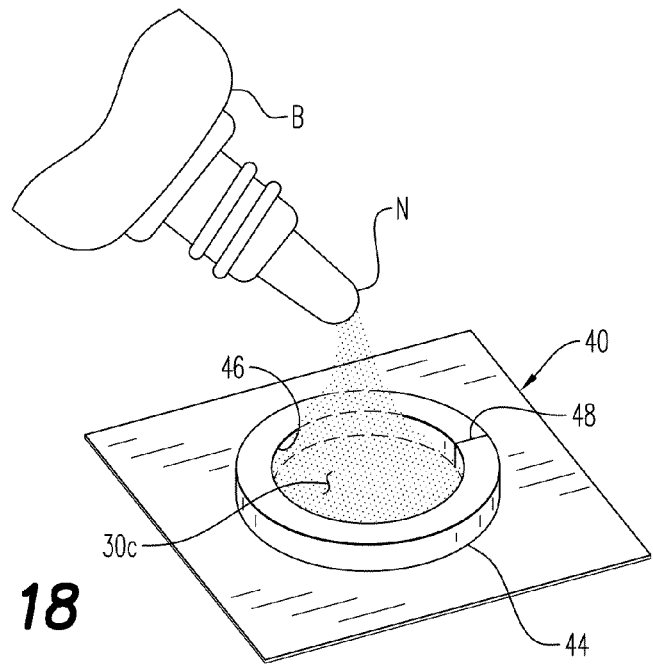
Figure 19:
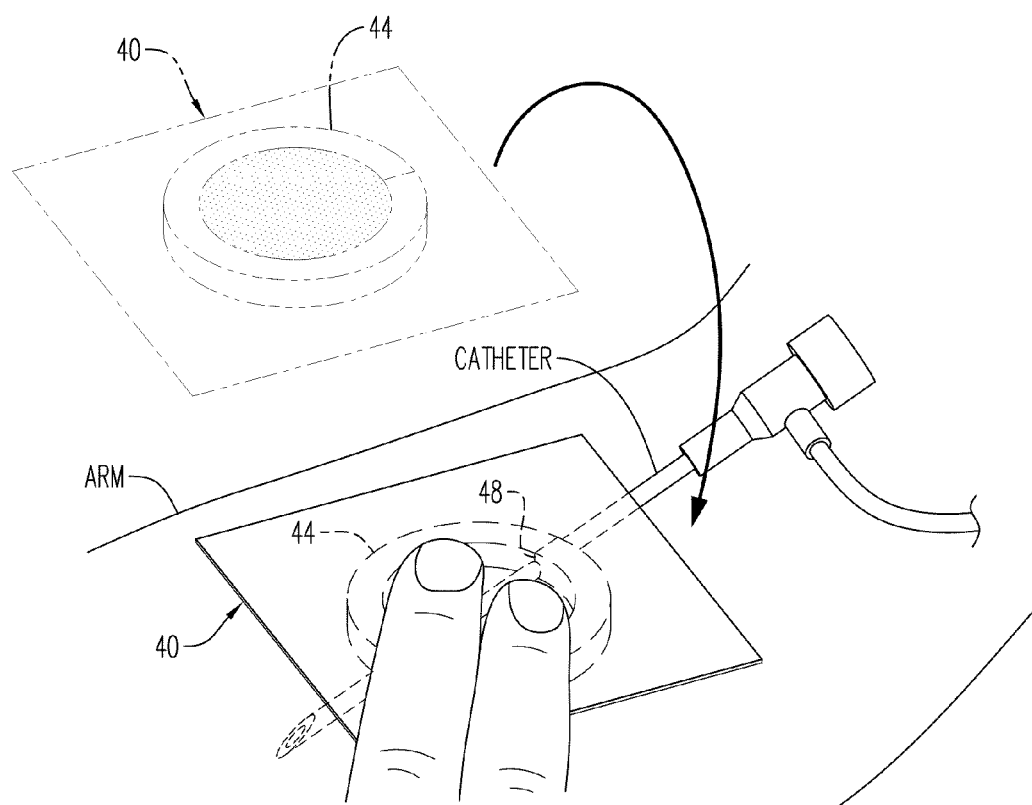
Figure 20:
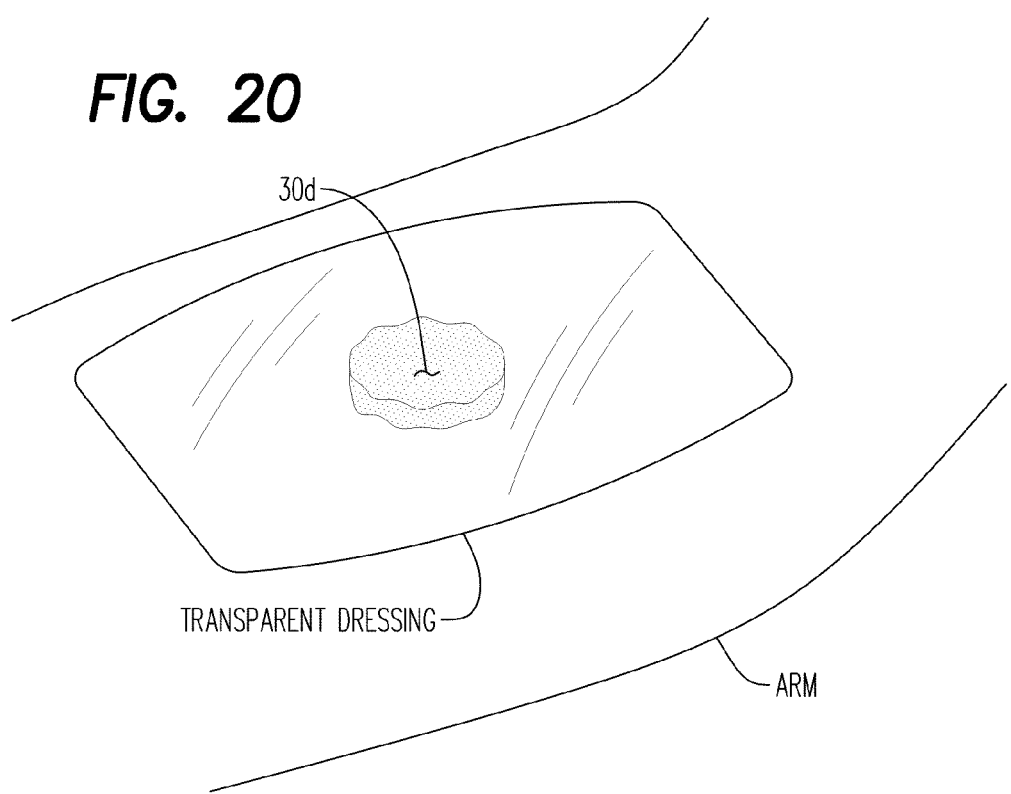
Figure 21:
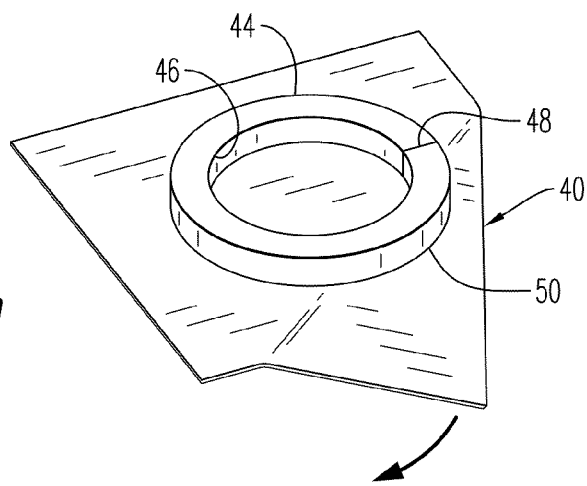
Figure 22:
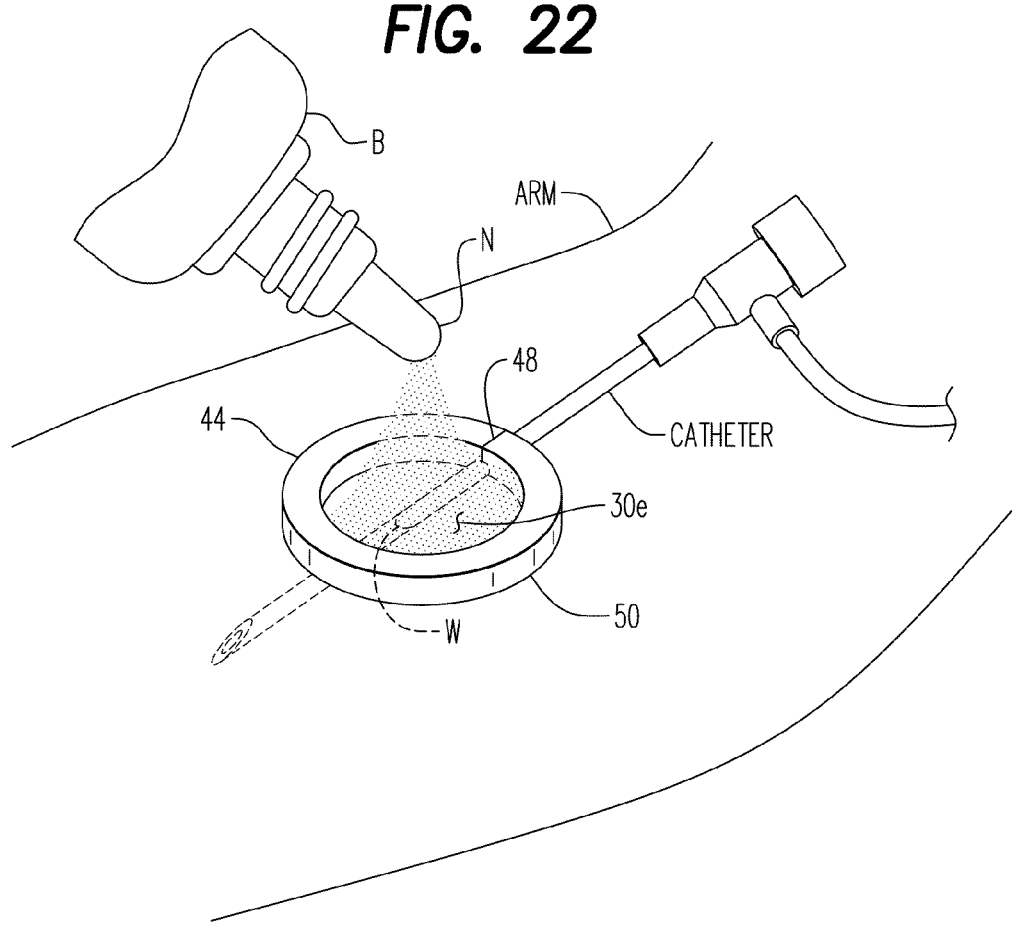
Figure 23:
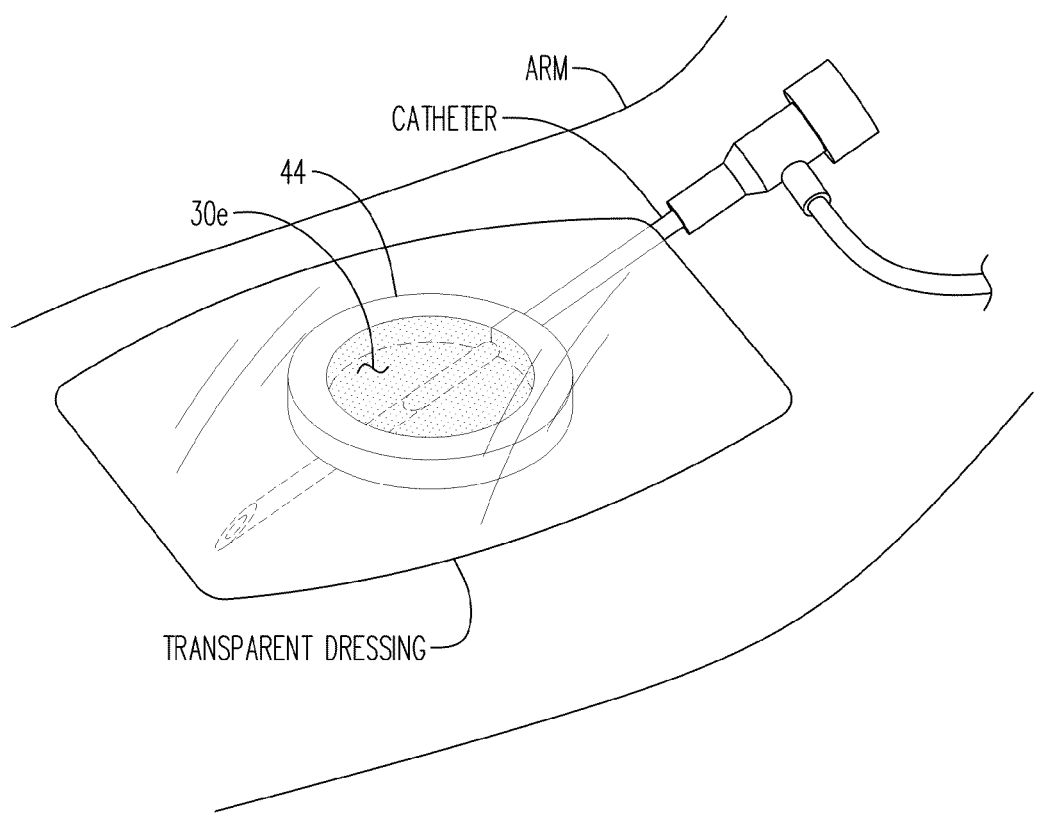
Figure 24:
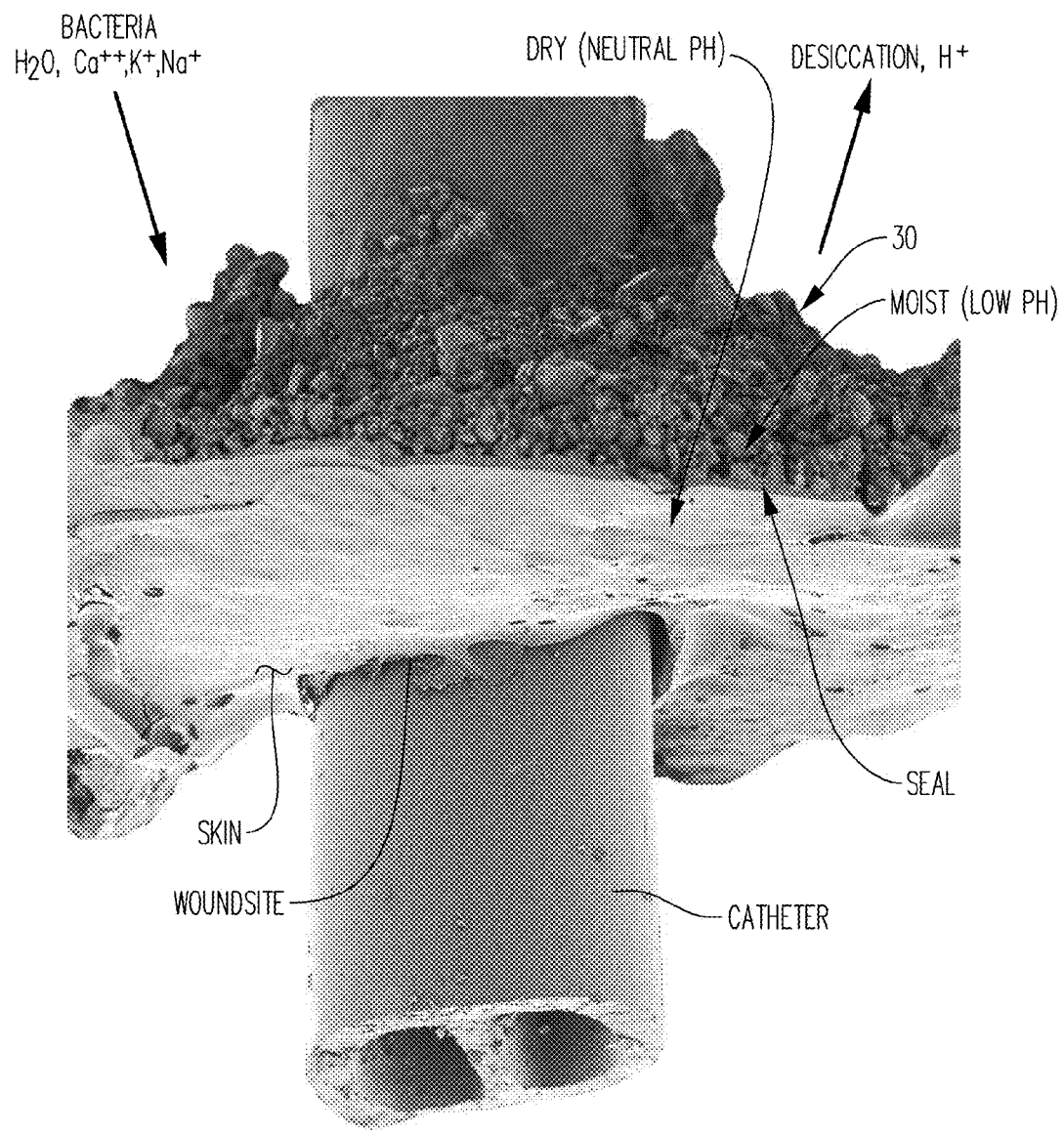

FIG. 4 is a section view in the direction of 4-4 in FIG. 1.
FIG. 4A is an enlargement of area 4A in FIG. 4.
FIG. 5 is a perspective view of FIG. 3.
FIG. 6 is a perspective view depicting installing the PCD embodiment of FIG. 1 onto the skin area around a catheter after removal of the cover as shown in FIG. 5.
FIG. 6A is a perspective view depicting installing another embodiment of the PCD onto the skin area around a catheter.
FIG. 7 is a perspective view showing filling a cavity formed by the PCD shown in FIG. 1 against the skin surrounding the catheter with an anhydrous hemostatic agent.
FIG. 7A is a perspective view showing direct application of the hemostatic agent around the catheter.
FIG. 8 is a perspective view showing removal of the catheter.
FIG. 9 is a prospective view showing application of finger pressure atop the hemostatic agent held within the PCD shown in FIG. 1.
FIG. 9A is a perspective view similar to FIG. 9 showing use of a third embodiment of a PCD.
FIG. 10 is a perspective view showing the preferred way of removing finger pressure from the hemostatic agent.
FIG. 11 is a perspective view showing a preferred transparent adhesive dressing installed over the PCD.
FIG. 11A is a perspective view showing a preferred transparent adhesive dressing installed over the hemostatic agent without use of the PCD.
FIG. 12 is a perspective view of the seal (scab) formed of hemostatic agent remaining after removal of the PCD.
FIGS. 13A to 13D depict the method associated with the installation of a catheter in conjunction with use of the PCD of FIG. 1 and the hemostatic agent.
FIG. 14 is a perspective view of the preferred embodiment of a powder containment device (PCD).
FIG. 15 is a top plan view of FIG. 14.
FIG. 16 is a bottom plan view of FIG. 14 showing the partial removal of an adhesive protective cover thereof.
FIG. 17 is a section view in the direction of arrows 17-17 in FIG. 14.
FIG. 17A is an enlargement of area 17a of FIG. 17.
FIGS. 18, 19 and 20 depict the method associated with the installation of the PCD of FIG. 14 associated with the installation of a catheter and the hemostatic agent.
FIGS. 21, 22 and 23 depict the preferred method of use of the PCD of FIG. 14 in conjunction with a catheter and the hemostatic agent during catheter insertion.
FIG. 24 is a photograph taken by a scanning electron microscope (SEM) of a cross-section view of the hemostatic agent deposited around an installed catheter. The seal shown is bone dry as required during sample preparation for SEM. The cracks seen under bone dry condition in the SEM photograph are not present in actual application.

Exemplary embodiments are illustrated in reference figures of the drawings. It is intended that the embodiments and figures disclosed herein are to be considered to be illustrative rather than limiting.

DETAILED DESCRIPTION OF THE INVENTION

Several in-vitro studies were conducted to show whether the anhydrous ferrate compound taught in U.S. Pat. No. 6,187,347 and distributed under the trademark PRO QR affords antimicrobial benefits with respect to well-known microbes.

I. Microbial Barrier Test/Strike Through Test for Pro QR (7 Days) [NAMSA, APPTEC]

Five USP microbes—S aureus, P aeruginosa, E coli, C albicans, A niger—and three other microbes—MRSA, MRSE, VRE—were used to test for growth using PRO QR against a control. The control showed growth after seven days. For PRO QR, the hemostatic agent of the present method, no growth for all the microbes after seven days showing the hemostatic agent to be an effective microbial barrier.

II. ASTM E 2149-01

This is a standard test method for determining antimicrobial activity of immobilized agents under dynamic contact conditions [AppTec].
24 hour assay without re-inoculation

|  | Initial contact CFU/ml | PRO QR Log reduction 1 hr | PRO QR Log reduction 24 hr | Control Log reduction 24 hr |
|---|---|---|---|---|
| S aureus | $3.8 \times 10^8$ | >5.6 | >5.6 | NR |
| E coli | $1.5 \times 10^8$ | 2.8 | >5.2 | NR |
| P aeruginosa | $1.3 \times 10^8$ | >5.1 | >5.1 | NR |
| MRSA | $1.7 \times 10^8$ | >5.2 | >5.2 | 0.6 |
| VRE | $2.9 \times 10^8$ | >5.5 | >5.5 | NR |
| MRSE | $1.4 \times 10^8$ | >5.1 | >5.1 | 0.5 |
| C albicans | $1.8 \times 10^8$ | NR | 4.1 | 0.1 |
| A niger | $1.3 \times 10^8$ | NR | 0.3 | NR |

NR = no reduction 7-day assay with re-inoculation (rechallenge) of MRSA every 24 hours

|  | PRO QR | Positive Control |
|---|---|---|
| Initial contact time, CFU/mL | $2.1 \times 10^6$ | $2.2 \times 10^6$ |
| Log reduction 24 hr | 5.3 | NR |
| Log reduction 48 hr | 5.3 | NR |
| Log reduction 72 hr | 5.3 | NR |
| Log reduction 96 hr | 5.3 | NR |
| Log reduction 120 hr | 5.3 | NR |
| Log reduction 144 hr | 5.3 | NR |
| Log reduction 168 hr | 5.3 | NR |

NR = no reduction 7 day assay with re-inoculation every 24 hours of MRSE and VRE
 PRO QR provide>log 4 reduction of MRSE and VRE after 7 days of daily re-inoculation
 control—no reduction in each of the 7 days.

III. Zone of Inhibition [STS-part of Ethox]

Microbes used—MRSA, MRSE, P aeruginosa and C albicans
PRO QR gave ZOI of 19 mm to 35 mm for all 4 microbes IV. Minimum Inhibitory Concentrations (MIC) of PRO QR [STS]

| Microbe | MIC (mg/ml) |
|---|---|
| MRSA | 20 |
| MRSE | 2.5 |
| P aeruginosa | 250 |
| C albicans | 31.25 |

V. Antimicrobial Effectiveness/Modified

USP 51 Preservative Testing [STS]

Microbes—MRSA, MRSE, *P aeruginosa* and *C albicans* PRO QR provided 5.9 to 7.5 log reduction in all four microbes at 1 hour, 1 day, 7 days and 14 days. There were no survivors of the four microbes at any time point.

VI. Biofilm Eradication with Calgary Biofilm Device [Innovotech]

Minimum Inhibitory Concentration (MIC) Breakpoints

|  | Pro QR | Gentamicin |
| --- | --- | --- |
| S. aureus | <25 mg/mL | <8 ug/mL |
| S. epidermidis | <25 mg/mL | <8 ug/mL |
| P. aeruginosa | <25 mg/mL | <8 ug/mL |

Minimum Bactericidal Concentration (MBC) Breakpoints

|  | Pro QR | Gentamicin |
| --- | --- | --- |
| MRS. aureus | <25 mg/mL | <16 ug/mL |
| MRS. epidermidis | <25 mg/mL | <8 ug/mL |
| P. aeruginosa | <25 mg/mL | <8 ug/mL |

Minimum Biofilm Eradication Concentration (MBEC) Breakpoints

|  | Pro QR | Gentamicin |
| --- | --- | --- |
| MRS. aureus | 75 mg/mL | 1024 ug/mL |
| MRS. epidermidis | <25 mg/mL | >1024 ug/mL |
| P. aeruginosa | 25 mg/mL | >1024 ug/mL |

Minimum Concentration that Kills Biofilms with Log R of 3 or Higher

|  | Pro QR | Gentamicin |
| --- | --- | --- |
| MRS. aureus | 75 mg/mL | 1024 ug/mL |
| MRS. epidermidis | 25 mg/mL | >1024 ug/mL |
| P. aeruginosa | 25 mg/mL | 64 ug/mL |

For MRS. *aureus*, a Log 10 Reduction greater than three occurred at concentrations of PRO-QR greater than or equal to 75 mg/mL. Gentamicin had a Log 10 Reduction greater than 3 at only 1024 ug/mL.

For MRS. *epidermidis*, a Log 10 Reduction greater than three occurred at all concentrations of PRO-QR. Gentamicin had no Log 10 Reduction greater than 3 at any concentration.

For *P. aeruginosa*, a Log 10 Reduction greater than four occurred at all concentrations of PRO-QR. Gentamicin had a Log 10 Reduction greater than three at concentrations of 256 ug/mL, 128 ug/mL and 64 ug/mL.

The above studies have substantiated the anti-microbial efficacy of the hemostatic agent, called PRO-QR, the anhydrous salt ferrate disclosed (powder or particulate) in U.S. Pat. No. 6,187,347 previously thought to be useful as a composition for arresting blood flow flowing from an open wound.

Protocol For Vascular Access Procedures

A protocol has been developed for implementing the method of the present invention utilizing the anhydrous ferrate and cationic exchange resin composition taught in U.S. Pat. No. 6,187,347, the entire teaching of which is incorporated herein by reference.

Referring now to the drawings, and firstly to FIGS. 1 to 4A, one embodiment of a powder containment device (PCD) is there shown generally at numeral 10 and is formed of a flexible dense foam or fiber pad 12 having a thickness of approximately 0.08" to 0.40" and a rectangular size of approximately 2" square. The preferred material is a closed cell polyurethane foam having a 3/16" thickness from Foam Innovations under the trademark CELLECT. The pad has a central hole 16 formed therethrough and a diagonal slit 18 to facilitate installation. The bottom or skin-facing surface of the PCD 12 has a removable protective cover 14 which, when released in the direction of the arrow in FIG. 5, exposes an adhesive layer 20 for temporary attachment of the pad 12 to a skin area of a patient.

As seen in FIG. 6, after the protective cover 14 has been removed, the pad 12 is positioned around a previously installed catheter which created a wound site W in a skin area, typically an arm of a patient. The slit 18 is opened to effect positioning of the hole 16 centrally around the wound site W and the catheter as seen in FIG. 7. Once the pad 12 has been adhesively attached to the skin area and the hole 16 is positioned generally symmetrically around the catheter, a quantity of the anhydrous ferrate compound 30 preferably in powder or granular form (also called the hemostatic agent), is dispensed from a nozzle N of a bottle B containing the ferrate compound 30. The ferrate compound is a hemostatic agent which includes an effective amount of a salt ferrate combined with an effective amount of an insoluble cation exchange material, the salt ferrate combining with blood or blood serum to form a trivalent $Fe^{+++}$ ion which promotes blood clotting and produces oxygen to reduce the bacteria level at the wound site W. The cation exchange material also forms a protective cover over the wound site as the trivalent $Fe^{+++}$ ion is formed.

After the anhydrous ferrate compound is poured into a cavity formed by the hole 16 and the underlying skin area, finger pressure is applied to compress and compact the ferrate powder as shown in FIG. 8 and FIG. 9. The downward preferably semi-occlusive finger pressure in the direction of arrow C in FIG. 9 is applied over the entire area of the hemostatic agent 30 after the catheter has been removed from the patient's arm in the direction of arrow B in FIG. 8. This semi-occlusive finger pressure is held for a time (typically 2 minutes for venous, 5 minutes for arterial) sufficient to allow the hemostatic agent to arrest blood flow and to form a seal over the wound site W. This continuous semi-occlusive pressure is typically held, where larger diameter catheters are used, for a longer length of time to effect coagulation of the blood flow at the wound site. As seen in FIG. 10, finger pressure should be released slowly by rolling the fingers away from the surface of the hemostatic agent 30 in the direction of arrow D.

As seen in FIG. 11, after the catheter has been removed and the hemostatic agent 30 has been held under finger pressure for a time sufficient to effect coagulation of the blood at the wound site, a preferably transparent dressing is adhesively applied over the entire arrangement and surrounding skin area for approximately a minimum of 2 days or until it is certain that the risk of internal infection of the patient is passed. After the transparent dressing and the pad 12 are removed, a small scab (seal) 30a shown in FIG. 12 will remain attached to the skin at and immediately around the wound site and should be left intact until the scab (seal) 30a simply falls off from the patient. This time period can last as long as three to four weeks and serves to insure protection of the wound site and preventing of further risk of internal infection through the wound site.

In FIG. 6A, another alternate embodiment of the PCD 12a is there shown wherein no installation slit is formed and wherein the installation of this pad 12a is made after the fluid has been disconnected from the associated fluid tubing and the pad 12a is simply passed over the catheter in the direction of arrow E. The adhesive surface 20a is then temporarily attached to the skin area while positioning the hole 16a centrally around the wound site W made by the catheter.

In FIG. 9A, another embodiment of a PCD 12a has only a half circle semi-cavity 16a for entrapping a quantity of hemostatic agent 30, followed by finger pressure in the direction of arrow C as previously described. This PCD embodiment 12b is particularly useful where the skin surface is inclined.

I.V. Catheter Insertion

The previously described protocol is associated with the removal of a catheter during which time the methodology of the present invention is then applied. However, as seen in FIGS. 13A to 13D, the protocol is also modified to be applied at the time of installation of the catheter. As seen in FIG. 13A, the catheter is first pierced at a point of entry through the skin area of the patient in the direction of the arrow. Thereafter, in FIG. 13B when the catheter has been positioned to be in proper fluid contact with a desired vein or vessel, the pad 12 is positioned around the catheter by separation of the slit 18 after the protective cover has been removed to expose the adhesive surface of the pad 12.

Once the pad 12 has been adhesively attached to the skin area as seen in FIG. 13C, with the hole 16 positioned centrally around the wound site made by the catheter, the anhydrous hemostatic agent 30 is poured into the cavity formed by the hole and the skin area. Finger pressure is applied as previously described to ensure that the blood flow, if any, has been fully arrested by the interaction of the blood or blood serum with the hemostatic agent. Thereafter, a preferably transparent dressing having a slit formed therethrough as shown in FIG. 13D is applied over the pad 12 and extending beyond the margins of the pad 12 sufficiently to effect adhesive attachment and protective covering of this arrangement during the time period that the catheter remains within the vein or artery of the patient.

Referring now to FIGS. 14 to 17A, a preferred embodiment of the PCD is shown generally at numeral 40 and includes a dense form or fiber pad 44 having an annular shape defining a central hole 46 which has a split 48 formed therethrough. The annular pad 44 is adhesively attached by an adhesive layer 50 to a removable protective cover 42 which, when released as shown in FIG. 16, exposes the adhesive layer 50 for temporary attachment of the annular pad 46 to a skin area of a patient.

Referring now to FIGS. 18 and 19, the preferred method of use of the PCD 40 is there shown. With the catheter inserted into a patient's arm or skin area so as to be in fluid communication with a vascular member within the arm, a quantity of the anhydrous ferrate compound 30, the hemostatic agent, is dispensed from the nozzle N of a bottle B containing the hemostatic agent 30c. After the hemostatic agent 30c is poured into a cavity formed by the hole 46 and the protective cover 42, the PCD 40 with the hemostatic agent 30c is then quickly flipped onto the arm as shown in FIG. 19 with the protective cover 42 remaining adhesively attached to the annular pad 44. The slit 48 facilitates holding the upper surface of the annular pad 44 against the skin around the catheter while applying semi-occlusive finger pressure against the hemostatic agent 30c as previously described. As seen in FIG. 20, after catheter is removed, a remaining hardened quantity of the hemostatic agent 30d is covered with a transparent dressing for healing of the catheter wound thereafter.

Referring now to FIGS. 21 to 23, an alternate and preferred utilization of the annular ring 44 is there shown. In conjunction with the installation of the catheter into the vein or artery of the patient, the annular pad 44 is removed from the protective cover 42 and then adhesively attached to the skin of the arm around the wound site W and the base of the catheter as facilitated by slit 48. The hemostatic agent is then poured into the cavity formed by the skin and the inner hole 46. Semi-occlusive finger pressure is applied atop the exposed surface of the hemostatic agent 30e as previously described and, after blood flow has ceased from the wound site W, a transparent dressing is applied over the annular ring 44 and the outwardly exposed portion of the catheter.

Sealed Hostile Environment Barrier

Note that use of the PCD is optimal because of its convenience. However, as shown in FIG. 7A, the same protection against systemic blood infections by way of vascular access procedures is achieved using the hemostatic agent (powder) without a PCD. One important aspect of the application of the hemostatic agent 30 is that it has a depth sufficient to absorb and interact with blood components at the skin surface, yet be sufficiently deep so that the outer surface of the hemostatic agent is dry. A pile depth of about 0.08" to 0.40" of the hemostatic agent 30 is sufficient and a depth of 0.19" to 0.40" is preferred. Dry powder is bactericidal due to the dehydration effect that the dry powder has upon skin surface bacteria. Thus, the pile of hemostatic agent piled atop the skin around the catheter may be viewed as being asymmetric, i.e., being moist and interactive with the blood components at the surface emerging from the wound site, yet dry at the outer surface of the powder to effect dehydration of bacteria and bactericidal effects.

Referring now to FIG. 24, the catheter is shown pierced through the epidural or skin layer and surrounded by a layer of hemostatic agent 30. This hemostatic agent 30 has been exposed to and interacted with blood serum which exits from the wound site and the catheter. The granules of the hemostatic agent 30 closest to the skin surface and around the catheter interact with the blood flow to form a tight seal. The blood will wick upwardly through a portion of the thickness of the hemostatic agent 30, but the upper layers thereof will remain dry. With finger pressure applied as previously described, hemostasis normally occurs in less than two minutes from the time of application of the hemostatic agent.

In vitro studies have shown that the hemostatic agent 30 creates a hostile environment against colonizing microbes based on the asymmetric dry/wet powder pile. On the outer surface of the dry hemostatic agent 30 above the seal, the pH is very low when hydrated, i.e., pH of about 2, while the pH under the seal is approximately neutral, i.e., about 7.4 pH. The polymer in the dry hemostatic agent above the seal rapidly desiccates the moisture in the bacteria while the potassium ferrate amalgamates the blood solids creating an occlusive barrier as shown. Bacterium full of water and salts comes in contact with the exposed surface of the hemostatic agent 30. Salts in the moist bacteria are exchanged for $H^+$, reducing the pH to 2.

Air Embolism Reduction

An important unexpected benefit of the present invention is that there is an air seal formed between the wound site, the catheter and the hemostatic agent that is so complete that a heretofore assumed risk of vascular access procedures in the form of air embolisms drawn into the vascular system due to the Bernoulli effect created by blood flow past the catheter tip are substantially reduced. Because the seal created by the interaction of the blood with the inner layers or granules of the hemostatic agent 30 is so complete, air embolisms have been substantially reduced or eliminated altogether.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. A method of reducing infections associated with vascular access procedures involving catheter insertion and removal comprising the steps of:
attaching a powder containment device (PCD) to a skin area, the PCD having a hole formed centrally therethrough adapted to at least partially surround the catheter at a wound site previously formed when the catheter was inserted into the skin area, said hole, in combination with the skin, defining an open cavity substantially wider than a width of the catheter;
positioning the skin area into a working orientation; at least partially filling said cavity with a hemostatic agent which includes an effective amount of a salt ferrate combined with an effective amount of an insoluble cation exchange material, said salt ferrate combining with blood to form a trivalent $Fe^{+++}$ ion promoting blood clotting and producing oxygen to reduce bacteria level at the wound site, said cation exchange material forming a protective cover over the wound site as said trivalent $Fe^{+++}$ ion is formed;
applying pressure against said hemostatic agent while removing the catheter from the wound site;
maintaining the pressure against said hemostatic agent for a time sufficient to arrest blood flow from the wound site;
releasing the pressure and covering the PCD with a transparent or translucent adhesive dressing.

2. A method of reducing infections associated with catheter installations comprising the steps of:
inserting the catheter through a skin area into a vein or artery and forming a wound site;
attaching a powder containment device (PCD) to the skin area, the PCD having a hole formed centrally therethrough substantially wider than a width of the catheter adapted to at least partially surround the catheter at the wound site, said hole, in combination with the skin area, defining an open cavity;
positioning the skin area in a generally horizontal orientation; at least partially filling said cavity with an anhydrous hemostatic agent which includes an effective amount of a salt ferrate combined with an effective amount of an insoluble cation exchange material, said salt ferrate combining with blood to form a trivalent $Fe^{+++}$ ion promoting blood clotting and producing oxygen to reduce bacteria level at the wound site, said cation exchange material forming a protective cover over the wound site as said trivalent $Fe^{+++}$ ion is formed;
applying pressure against said hemostatic agent;
maintaining the pressure against said hemostatic agent for a time sufficient to arrest blood flow from the wound site;
releasing the pressure and covering the PCD with a transparent or translucent adhesive dressing.

3. A method of reducing infections associated with vascular access procedures involving catheter insertion and removal comprising the steps of:
positioning a skin area into a working orientation;
pouring a quantity of an anhydrous hemostatic agent sufficient to produce an asymmetric dry/wet powder pile around a wound site made by insertion or removal of a catheter into or from a vascular member, the hemostatic agent including an effective amount of a salt ferrate combined with an effective amount of an insoluble cation exchange material, said salt ferrate combining with blood to form a trivalent $Fe^{+++}$ ion promoting blood clotting and producing oxygen to reduce bacteria level at the wound site, said cation exchange material forming a protective cover over the wound site as said trivalent $Fe^{+++}$ ion is formed;
applying semi-occlusive pressure against said hemostatic agent and maintaining the pressure against said hemostatic agent for a time sufficient to arrest blood flow from the wound site;
releasing the pressure and covering said hemostatic agent with a transparent or translucent adhesive dressing.

4. A method of reducing air embolisms associated with vascular access procedures involving catheter installations comprising the steps of:
inserting the catheter through the skin area into the vein or artery and forming a wound site;
attaching a powder containment device (PCD) to the skin area, the PCD having a hole formed centrally therethrough substantially wider than a width of the catheter adapted to surround the catheter at the wound site, said hole, in combination with the skin area, defining an open cavity;
positioning the skin area in a generally horizontal orientation;
at least partially filling said cavity with an anhydrous hemostatic agent which includes an effective amount of a salt ferrate combined with an effective amount of an insoluble cation exchange material, said salt ferrate combining with blood to form a trivalent $Fe^{+++}$ ion promoting blood clotting and producing oxygen to reduce bacteria level at the wound site, said cation exchange material forming a protective sealing cover over the wound site as said trivalent $Fe^{+++}$ ion is formed;
applying pressure against said hemostatic agent;
maintaining the pressure against said hemostatic agent for a time sufficient to arrest blood flow from the wound site;
releasing the pressure and covering the PCD with a transparent or translucent adhesive dressing.

5. A method of reducing air embolisms associated with vascular access procedures involving catheter insertion and removal comprising the steps of:
positioning a skin area into a working orientation;
pouring a quantity of an anhydrous hemostatic agent sufficient to produce an asymmetric dry/wet powder pile around a wound site made by insertion or removal of a catheter into or from a vascular member, the hemostatic agent including an effective amount of a salt ferrate combined with an effective amount of an insoluble cation exchange material, said salt ferrate combining with blood to form a trivalent $Fe^{+++}$ ion promoting blood clotting and producing oxygen to reduce bacteria level at the wound site, said cation exchange material forming a protective sealing cover over the wound site as said trivalent $Fe^{+++}$ ion is formed;

applying semi-occlusive pressure against said hemostatic agent and maintaining the pressure against said hemostatic agent for a time sufficient to arrest blood flow from the wound site;

releasing the pressure and covering said hemostatic agent with a transparent or translucent adhesive dressing.

* * * * *